US008968781B2

(12) United States Patent
Gowan, Jr. et al.

(10) Patent No.: US 8,968,781 B2
(45) Date of Patent: Mar. 3, 2015

(54) THERAPEUTIC COMPOSITIONS

(75) Inventors: Walter G. Gowan, Jr., Birmingham, AL (US); Dennis D. Keith, Arlington, MA (US); Sandra O'Connor, Mont Vernon, NH (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 1921 days.

(21) Appl. No.: 11/912,833

(22) PCT Filed: Apr. 27, 2006

(86) PCT No.: PCT/US2006/016030
§ 371 (c)(1),
(2), (4) Date: Oct. 26, 2007

(87) PCT Pub. No.: WO2006/118948
PCT Pub. Date: Nov. 9, 2006

(65) Prior Publication Data
US 2008/0213366 A1    Sep. 4, 2008

Related U.S. Application Data

(60) Provisional application No. 60/676,146, filed on Apr. 29, 2005.

(51) Int. Cl.
A61K 9/36       (2006.01)
A61K 31/545     (2006.01)
A61K 9/16       (2006.01)

(52) U.S. Cl.
CPC ............ *A61K 31/545* (2013.01); *A61K 9/1617* (2013.01); *A61K 9/1652* (2013.01)
USPC ........... 424/480; 424/494; 424/474; 424/490; 514/8; 514/196; 514/14

(58) Field of Classification Search
None
See application file for complete search history.

(56) References Cited

U.S. PATENT DOCUMENTS

| | | |
|---|---|---|
| 3,725,400 A | 4/1973 | Voser |
| 3,886,125 A | 5/1975 | Chromecek |
| 4,188,373 A | 2/1980 | Krezanoski |
| 4,327,210 A | 4/1982 | Montavon et al. |
| 4,525,339 A | 6/1985 | Behl et al. |
| 4,525,399 A | 6/1985 | Fields |
| 4,574,152 A | 3/1986 | Noble |
| 4,616,008 A | 10/1986 | Hirai et al. |
| 4,722,941 A | 2/1988 | Eckert et al. |
| 4,732,753 A | 3/1988 | Füller |
| 4,902,501 A | 2/1990 | Bandi et al. |
| 5,190,748 A * | 3/1993 | Bachynsky et al. ........ 424/78.08 |
| 5,260,292 A | 11/1993 | Robinson et al. |
| 5,318,781 A | 6/1994 | Shah et al. |
| 5,472,704 A | 12/1995 | Santus et al. |
| 5,783,561 A | 7/1998 | Horwitz et al. |
| 5,852,004 A | 12/1998 | Barritault et al. |
| 5,856,474 A | 1/1999 | Ascher et al. |
| 5,861,508 A | 1/1999 | Ludescher et al. |
| 5,968,253 A | 10/1999 | Poser et al. |
| 5,968,895 A | 10/1999 | Gefter et al. |
| 5,994,340 A | 11/1999 | Maiti et al. |
| 6,004,583 A | 12/1999 | Platé et al. |
| 6,008,228 A | 12/1999 | Bailey et al. |
| 6,017,513 A | 1/2000 | Betbeder et al. |
| 6,025,352 A | 2/2000 | Cho et al. |
| 6,063,917 A | 5/2000 | Ascher et al. |
| 6,071,447 A | 6/2000 | Bootman et al. |
| 6,093,813 A | 7/2000 | Ascher et al. |
| 6,214,378 B1 | 4/2001 | Tanida et al. |
| 6,232,306 B1 | 5/2001 | Hebeisen et al. |
| 6,248,360 B1 | 6/2001 | Choi et al. |
| 6,315,981 B1 | 11/2001 | Unger |
| 6,458,387 B1 | 10/2002 | Scott et al. |
| 6,458,772 B1 | 10/2002 | Zhou et al. |
| 6,465,626 B1 | 10/2002 | Watts et al. |
| 6,693,095 B2 | 2/2004 | Ascher et al. |
| 6,727,243 B1 | 4/2004 | Jennewein et al. |
| 6,794,490 B2 | 9/2004 | Hill et al. |
| 6,902,743 B1 | 6/2005 | Setterstrom et al. |
| 6,911,525 B2 | 6/2005 | Hill et al. |
| 6,974,799 B2 * | 12/2005 | Lintner ..................... 514/18 |
| 7,153,524 B2 * | 12/2006 | Yoshihara et al. ......... 424/486 |
| 7,262,268 B2 | 8/2007 | Morytko et al. |
| 7,527,807 B2 * | 5/2009 | Choi et al. ................. 424/488 |
| 2002/0004499 A1 | 1/2002 | Rudnic et al. |

(Continued)

FOREIGN PATENT DOCUMENTS

| EP | 0 213 552 | 3/1987 |
|---|---|---|
| EP | 0 207 624 B1 | 3/1991 |

(Continued)

OTHER PUBLICATIONS

Andega et al., *J. Controlled Release* 77:17-25 (2001).
Arima et al., *J. Pharm. Sci.* 90(6):690-701 (2001).
*Carbapenem*, IMS R&D Focus, Feb. 19, 2001, available at DIALOG, File No. 445.
Cho et al., *J. Pharm. Sci.* 93(3):612-620 (2004).
Crowley et al., *Curr. Opin. Drug Disc. Dev.* 4(1):73-80 (2001).
Dimitrijevic et al., *J. Pharm. Pharmacol.* 52:157-162 (2000).
Drewe et al., *Br. J. Pharmacol.* 108:298-303 (1993).
Eley et al., *AAPS PharmsciTech 2001* 2(3), Article 19 (2001).
Gershanik et al., *Eur. J. Pharm. Biopharm.* 50:179-188 (2000).
Guarini et al., *Arch. Int. Pharmacodyn.* 271:4-10 (1984).
Guzman et al., *PRHSJ* 9(2):155-159 (1990).
Healey, *Drug Delivery to the Gastrointestinal Tract*, Ch. 7, Hardy et (Continued)

*Primary Examiner* — Suzanne Ziska
(74) *Attorney, Agent, or Firm* — Lando & Anastasi LLP

(57) ABSTRACT

The present invention provides oral formulations of poorly bioavailable and/or poorly absorbable, and/or poorly water soluble therapeutic agents. The invention features pharmaceutical composition including a biopolymer, a therapeutic agent, for example an antimicrobial agent such as ceftriaxone, and an absorption enhancer, for example a polyoxyethylene alkyl ether absorption enhancer. Methods of making and using the pharmaceutical compositions is also described.

26 Claims, 2 Drawing Sheets

(56) References Cited

U.S. PATENT DOCUMENTS

| | | |
|---|---|---|
| 2002/0051820 A1 | 5/2002 | Shell et al. |
| 2002/0119195 A1 | 8/2002 | Sen et al. |
| 2003/0083240 A1 | 5/2003 | Finn et al. |
| 2004/0067878 A1 | 4/2004 | Hill et al. |
| 2004/0131665 A1 | 7/2004 | Wepfer |
| 2004/0208936 A1 | 10/2004 | Chorin et al. |
| 2005/0020537 A1 | 1/2005 | Leung et al. |
| 2005/0037071 A1 | 2/2005 | Cao et al. |

FOREIGN PATENT DOCUMENTS

| | | |
|---|---|---|
| EP | 0 526 862 B1 | 2/1996 |
| JP | 2000-302621 | 10/2000 |
| WO | WO 99/31106 | 6/1999 |
| WO | WO 99/45010 | 9/1999 |
| WO | WO 01/01959 | 1/2001 |
| WO | WO 01/02401 | 1/2001 |
| WO | WO 01/32218 | 5/2001 |
| WO | WO 01/97851 | 12/2001 |
| WO | WO 02/04012 | 1/2002 |
| WO | WO 2004/066976 | 8/2004 |
| WO | WO 2004/073695 | 9/2004 |
| WO | WO 2005/018618 | 3/2005 |
| WO | WO 2006/118948 A2 | 11/2006 |

OTHER PUBLICATIONS al., eds., Ellis Horwood, Chichester (1989).
International Search Report and Written Opinion issued in international stage for Application No. PCT/US2006/016030 (subject application), dated Mar. 23, 2007.
Jiraskova, *Curr. Opin. Investig. Drugs* 2(2):209-211 (2001).
JP 2000302621 Patent Abstracts of Japan, vol. 2000, No. 13.
Junginger et al., *J. Controlled Release* 62:149-159 (1999).
Kato et al., *Drug Metab. Pharm. Sci.* 17(4):363-366 (2002).
Kaur et al., *Drug Dev. Indus. Pharm.* 28(4):353-369 (2002).
Kompella et al., *Adv. Drug Delivery Rev.* 46:211-245 (2001).
Lang Bowe et al., *Proc. Natl. Acad. Sci USA* 94(22):12218-12223 (1997).
Leone-Bay et al., *Med. Res. Rev.* 20(2):169-186 (2000).
Lindmark et al., *J. Pharmacol. Exp. Ther.* 284(1):362-369 (1998).
Lundin et al., *J. Pharmacol. Exp. Ther.* 282(2):585-590 (1997).
Lyons et al., *Int. J. Pharm.* 199:17-28 (2000).
Miyamoto et al., *J. Pharm. Sci.* 72(6):651-654 (1983).
Mlynek et al., *Int. J. Pharm.* 197:13-21 (2000).
Palin et al., *Int. J. Pharm.* 33:99-104 (1986).
Pouton, *Eur. J. Pharm. Sci.* 11 Suppl. 2:S93-S98 (2000).
Ritschel et al., *Meth. Find Exp. Clin. Pharmacol.* 11(4):281-287 (1989).
Sakuma et al., *Adv. Drug Delivery Rev.* 47:21-37 (2001).
Sayani et al., *Crit. Rev. Ther. Drug Carrier Syst.* 13(1&2):85-184 (1996).
Sekine et al., *J. Pharmacobio-Dyn.* 8:286-295 (1985).
Soderholm et al., *Digestive Dis. Sci.* 43(7):1547-1552 (1995).
Sutton et al., *Pharm. Res.* 10(10):1516-1520 (1993).
Swenson et al., *Pharm. Res.* 11(10):1501-1504 (1994).
Takahashi et al., *Pharm. Res.* 11(3):388-392 (1994).
Thanou et al., *Pharm. Res.* 17(1):27-31 (2000).
Uchiyama et al., *J. Pharm. Pharmacol.* 51:1241-1250 (1999).
Ueda et al., *J. Pharm. Sci.* 72(4):454-458 (1983).
Walters et al., *J. Pharm. Pharmacol.* 33:207-213 (1981).
Wasan, *Drug Dev. Indus. Pharm.* 27(4):267-276 (2001).
Yoshitomi et al., *J. Pharm. Pharmacol.* 39:887-891 (1987).
Yu et al., *Pharm. Res.* 16(12):1812-1817 (1999).
Beskid et al., "Enteral, Oral, and Rectal Absorption of Ceftriaxone Using Glyceride Enhancers," *Chemotherapy* 34: 77-84 (1988).

* cited by examiner

THERAPEUTIC COMPOSITIONS

CROSS-REFERENCE TO RELATED APPLICATIONS

This application is a national stage application under 35 U.S.C. §371 of International Application No. PCT/US2006/016030, filed Apr. 27, 2006, which claims the benefit under 35 U.S.C. §119 of U.S. Provisional Application No. 60/676,146, filed Apr. 29, 2005, which is hereby incorporated by reference in its entirety.

TECHNICAL FIELD

This invention relates to pharmaceutical compositions.

BACKGROUND

Many therapeutic agents exhibit poor oral bioavailability and or absorption and therefore are administered by injection. For example, cephalosporin is the general term for a group of antibiotic derivatives of cephalosporin C, which is obtained from the fungus *Cephalsporium acremonium*. First generation cephalosporins and most second generation cephalosporins are functional in oral dosage forms. However, in many instances the third generation cephalosporins have poor oral bioavailability and therefore are often administered by injection.

SUMMARY

Oral formulations of poorly available and/or poorly water soluble therapeutic agents are described herein, for example a pharmaceutical composition including ceftriaxone. In some instances, the compositions described herein have improved systemic uptake, e.g., improved uptake into the plasma of a subject. In some instances, the compositions described herein have improved stability of the therapeutic agent and/or enhanced pharmacokinetic and pharmacodynamic profiles and/or improved post-antibiotic effects.

In one aspect, the invention features pharmaceutical composition including a biopolymer, a therapeutic agent, for example an antimicrobial agent such as ceftriaxone, and an absorption enhancer, for example a polyoxyethylene alkyl ether absorption enhancer.

In some instance, the therapeutic agent is poorly bioavailable and/or poorly absorbable, and/or poorly water soluble. For example, in some instances the bioavailability or absorption of the therapeutic can be improved when formulated in one of the compositions described herein.

Examples of therapeutic agents include antimicrobial agents, (e.g., antibiotics such as ceftriaxone), anti-inflammatory agents, anti-neoplastic agents, anti-pyretic agents, metabolic agents, polypeptides, antibodies, neucleic acids, hormones, or other therapeutic agents and combinations thereof.

Examples of antimicrobial agents include, for example, cephalosporins, glycopeptides, penicillins (e.g., piperacillin or amoxicillin), monobactams (e.g., aztreonam or carumonam), oxazolidinones, lipopeptides (e.g., daptomycin), carbapenems (e.g., meropenem, imipenem, MK0826, R-115, 685, J-114,870 or CP5068), aminoglycosides, β-lactamase inhibitors and combinations thereof.

In some instances, the cephalosporin can be ceftiofur, cefipime, cefixime, cefoperazone, cefotaxime, cefpodoxime, ceftazidime, ceftizoxime, ceftriaxone, cefpirome, cefclidin, cefinenoxime, cefozoprane, or combinations thereof. In some instances, the cephalosporin is a novel cephalosporin, such as CAB. In some preferred embodiments, the cephalosporin is ceftriaxone.

In some instances, the antimicrobial is an aminoglycoside, for example amikacin, gentamicin, tobramycin, polymixin-B, streptomycin, kanamycin or combinations thereof.

The therapeutic agent can be, for example a glycopeptide such as vancomycin, dalbavancin, oritavancin or combinations thereof.

The biopolymer can be, for example, a neutral or an anionic polymer such as carageenan. For example, the biopolymer can be a cellulosic polymer such as hydroxyethyl cellulose, methyl cellulose, hydroxypropyl cellulose, hydroxypropyl methyl cellulose, a carbopol, or a polycarbophil. In some preferred embodiments the biopolymer is carageenan or a polycarbophil.

In some instances, the biopolymer is a cationic polymer such as carageenan.

In some embodiments, the absorption enhancer is a monoglyceride of a $C_{12}$-$C_{18}$ fatty acid, a diglyceride of a $C_6$-$C_{18}$ fatty acid, a triglyceride of a $C_{12}$-$C_{18}$ fatty acid, or a mixture thereof, for example, gelucire.

In some preferred embodiments, the absorption enhancer is a polyoxyethylene alkyl ether, a mono-, di-, or tri-glyceride of a fatty acid, or a salt of a fatty acid. In more preferred embodiments, the absorption enhancer is a polyoxyethylene alkyl ether. The polyoxyethylene alkyl ether can have a plurality of alkyl chain lengths, for example, between 4 and 23 units, for example a plurality of alkyl chain lengths from 10 to 15 units.

In some embodiments, the polyoxyethylene alkyl ether is linked to a fatty acid or a fatty alcohol, for example a fatty acid or fatty alcohol having from about 10 to about 18 carbons (e.g., from about 12 to about 16 carbons).

In some embodiments, a fatty acid or fatty alcohol of 10-18 carbons is linked to a polyoxyethylene group of 8-18 units. For example, a fatty acid or fatty alcohol of 12-16 carbons is linked to a polyoxyethylene group of 10-15 units.

In some embodiments, the polyoxyethylene alkyl ether is laureth 12, ceteth 12, ceteth 15, or oleth 10.

In some embodiments, the ratio of enhancer to therapeutic agent (e.g., antimicrobial agent such as ceftriaxone) is between about 10:1 to about 1:2. For example, the ratio can be from about 6:1 to about 1:1, such as about 4:1 or about 2:1.

In some embodiments, the pharmaceutical composition also includes a binder.

In some embodiments, the pharmaceutical composition is substantially free of a cationic binding agent.

In some embodiments, the pharmaceutical composition is substantially free of a cationic biopolymer.

In some embodiments, the bioavailability of the antimicrobial is at least about ten times greater in the pharmaceutical composition than a formulation substantially free of an enhancer. For example, the bioavailability of the antimicrobial is at least about 20 times greater.

In some embodiments, the polymer is a polycarbophil, a carageenen, or a cellulosic and the absorption enhancer is a polyoxyethylene alkyl ether, e.g., laureth 12, ceteth 12, ceteth 15, or oleth 10.

In some embodiments, the absorption enhancer is a ceteth and the biopolymer is a carbopol.

In some embodiments, the absorption enhancer is ceteth 12 and the biopolymer is polycarbophil.

In some embodiments, the absorption enhancer is ceteth 12 and the biopolymer is hydroxyethyl cellulose.

In some embodiments, the therapeutic agent is ceftriaxone, the absorption enhancer is a polyoxyethylene alkyl ether, and the biopolymer is a polycarbophil, a carageenen, or a cellulosic. For example, the polyoxyethylene alkyl ether is laureth 12, ceteth 12, ceteth 15, or oleth 10, and the biopolymer is carageenen or a polycarbophil.

In some embodiments, the bioavailability of the therapeutic agent in a pharmaceutical composition described herein is at least about 10 times greater than the bioavailability of the therapeutic agent alone, for example at least about 20 greater than the bioavailability of the therapeutic agent alone.

In some embodiments, the invention includes an enterically coated tablet or capsule including a pharmaceutical composition described herein.

In some embodiments, the invention includes an enterically coated bead or particle including a pharmaceutical composition described herein. In general, the coated bead or particle is suitable for a tablet or capsule dosage form. The bead or particle can be coated with, for example, an enteric coating or polymer such as hydroxyethyl cellulose, hydroxypropyl methyl cellulose, etc. In some embodiments the enterically coated bead or particle is suitable for mixing with a palatable diluent for the preparation of an oral suspension.

In some embodiments, the invention features an enterically coated tablet, capsule, bead or particle a pharmaceutical composition described herein and an additional therapeutic agent where the components are physically separated within the dosage form. In other embodiments, the invention features an enterically coated tablet, capsule, bead or particle including a pharmaceutical composition described herein and an additional therapeutic agent where the components are intimately mixed within the dosage form.

The pharmaceutical compositions described herein can be formulated, for example, as a solid, semi-solid, or liquid.

In some embodiments, the invention includes a method of making a pharmaceutical composition described herein. The method includes hydrating the biopolymer; combining the antimicrobial with the hydrated biopolymer to form a complex; and combining the complex with the enhancer to provide a pharmaceutical composition described herein.

The pharmaceutical compositions described herein can also be made using other methods, for example, spray drying/congealing, and forming emulsions of one or more components of the pharmaceutical composition.

In some embodiments, the invention features a method of treating a subject (e.g., a mammal such as a human or a companion animal) including administering to the animal the pharmaceutical composition described herein.

DESCRIPTION OF DRAWINGS

Like reference symbols in the various drawings indicate like elements.

DETAILED DESCRIPTION

Figure 1:
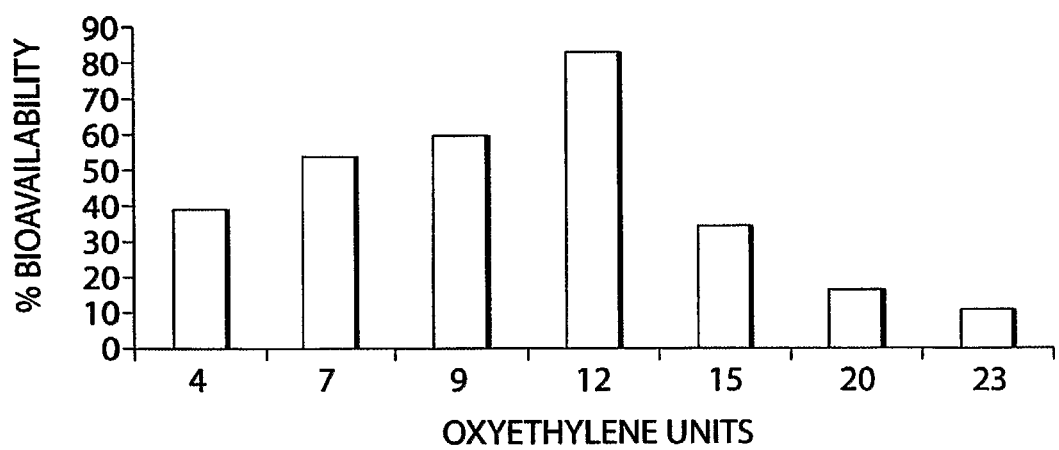
FIG. 1 is a graph depicting % bioavailability of Laureth analog enhancers in rats.

As used herein, terms have their common meaning unless otherwise specified.

As used herein, the term "poorly absorbable" is used to describe a therapeutic agent that exhibits low bioavailability in oral or other non-parenteral dosage forms. In some instances, the therapeutic agent is poorly absorbable due to relatively high hydrophilicity and/or ionization properties of the therapeutic agent (e.g., antimicrobial agent). The therapeutic agent can be positively charged, negatively charged, neutral, zwiterionic or amphiphilic.

As used herein, the term "oral absorption" is used to describe the manner in which the compositions described herein are delivered to the subject and the active ingredients absorbed into the blood. Typically, the composition is administered orally and the therapeutic agent of the composition then crosses a mucosal membrane of the gastrointestinal tract, preferably in the intestines. However, other methods of contacting the compositions of the present invention with the mucosal membrane of the gastrointestinal tract may be used.

Therapeutic compositions are described herein. In general, the therapeutic compositions include a therapeutic agent, for example a poorly absorbable or poorly water soluble agent, a biopolymer, and an absorption enhancer, such as a polyoxyethylene alkyl ether. In many instances, the compounds have improved absorption characteristics, resulting in increased bioavailability. In particular, it has been discovered that certain classes of absorption enhancers provide compositions with improved bioavailability of therapeutic agents. In some instances, these absorption enhancers can be administered in compositions having a reduced ratio of absorption enhancer to therapeutic agent, resulting in a dosage with reduced bulk.

Therapeutic Agents:

In general, the compositions described herein can include any therapeutic agent, in particular any poorly bioavailable or poorly absorbable agent.

Examples of therapeutic agents include antimicrobial agents (e.g., antibacterial agents, anti-fungal agents, anti-viral agents, etc.), anti-inflammatory agents, anti-neoplastic agents, anti-pyretic agents, metabolic agents, polypeptides, antibodies, nucleic acids, hormones, or other therapeutic agents.

Examples of antimicrobial agents include cephalosporins, aminoglycosides, carbapenems, β-lactamase inhibitors, anti-fungals, penicillins, lipopeptides, glycopeptides, monobactams, and oxazolidinones.

In instances where the antimicrobial agent is a cephalosporin, examples of cephalosporins include, for example, ceftiofur, cefipime, cefixime, cefoperazone, cefotaxime, cefpodoxime, ceftazidime, ceftizoxime, cefiriaxone, cefinenoxime, cefozoprane, cefpirome, and cefclidin. In addition, cephalosporins that are active against methicillin resistant *Staph. aureus* (MRSA), and which are in development stages such as RO 65-5788 (U.S. Pat. No. 6,232,306, hereby incorporated by reference in its entirety), RWJ-54428 (U.S. Pat. No. 6,025,352, hereby incorporated by reference in its entirety), RWJ-333441 (Curr. Opin. Invest. Drugs (2001); 2(2) 209-211, hereby incorporated by reference) can also be incorporated into the compositions described herein. Additionally, cephalosporins such as those described in U.S. Pat. No. 6,693,095 (hereby incorporated by reference) are useful. In some instances the cephalosporin is ceftriaxone, such as described in U.S. Pat. No. 4,327,210.

Other examples of antimicrobial agents include aminoglycosides, such as, for example amikacin, gentamicin, tobramycin, polymixin-B, streptomycin, and kanamycin. The agent may in some embodiments be a glycyldline.

Still other examples of antimicrobial agents are carbapenems, such as for example, meropenem, imipenem, MK0826 (Invanz, WO 99/45010, hereby incorporated by reference), R-115,685 (Sankyo, WO 01/02401 hereby incorporated by reference), J-114,870 (Banyu, WO 99/31106 hereby incorporated by reference) and CP-5068 (Meiji, see R&D Focus, Feb. 19, 2001; IMS World Publications).

In some instances, the therapeutic agent is a lactamase inhibitor (e.g., β-lactamase inhibitor) a such as tazobactam, oxapenem, clavulanic acid, sublactam, or, for example, Zosyne which is a combination of tazobactam and pipericillin marketed by Wyeth-Ayerst.

Lipopeptides such as daptomycin and A54145 are still other examples of therapeutic agents. Analogs of daptomycin and A54145 are disclosed in U.S. Ser. Nos. 09/738,742, 09/737,908, 10,213,218 and 10,213,389, and U.S. Pat. No. 6,794,490, hereby incorporated by reference in their entirety, and are also useful therapeutic agents of the present invention.

Additional antimicrobials include glycopeptides such as vancomycin, dalbavancin and oritavancin, monobactamns such as aztreonam or carumonam.

In some embodiments the therapeutic agent is an antifungal agent, such as for example, amphotericin B, echinocandins and cancidas.

In other embodiments, the therapeutic agent is a penicillin, such as, for example, piperacillin and amoxicillin.

Biopolymers:

As used herein, the term "biopolymer" shall mean a biologically compatible polymer which can be naturally occurring or synthetic and shall also include liposomes and clathrates. The biopolymer can be a neutral, an anionic polymer, or a cationic polymer.

In general, the pharmaceutical compositions can include any biopolymer that is not toxic to the subject to be treated, and provides for the desired characteristics of the pharmaceutical composition. In some instances, biopolymers that are mucoadhesive and/or swellable biopolymers are preferred. Exemplary biopolymers include, but are not limited to carrageenans, carbopols, polycarbophils, cellulosics (e.g., hydroxyethyl cellulose, methyl cellulose, hydroxypropyl cellulose or carboxymethylcellulose), pectins, chondroitin sulfate, polymethacrylic acid, xylan, hyaluronic acid, chitin, chitosan, sodium alginates, polysaccharides, polypropylene glycols, polyethylene glycols, polyacetates, liposomes, fatty acid complexes, cyclodextrins, cycloamyloses, clathrates, cycloalkyl amyloses, polyxylose, gellan gums and polylactic acids.

As used herein, the term "mucoadhesive" means a composition that binds to the mucous membrane or a mucin layer of a biological membrane. In some instances, a mucoadhesive biopolymer can be used to administer a therapeutic agent through a mucin layer of a biological membrane.

As used herein, the term "swellable" refers to a compound or composition that can become swollen, for example in an aqueous environment such as the stomach or intestinal tract of a subject.

Carrageenan is the general term used to describe hydrophilic polysaccharides extracted from a number of closely related species of red seaweeds that are highly sulfated, linear molecules having a galactose backbone. There are three different types of carrageenan, Kappa, Lambda and Iota, which are differentiated by the amount of 3,6-anhydrogalactose residues and number and position of the sulfate groups. For example, the following carrageenans can be obtained from FMC Biopolymer: Gelcarin® GP 379 (Iota) and Gelcarin® GP 911 (Kappa).

The preferred carrageenan for certain compositions of the invention is a carrageenan having a low calcium content, i.e. a calcium content of from about 0 to about 4% (preferably 3.6%), more preferably about 0-2%, and most preferably about 0.1-1% calcium by weight. The most preferred carrageenan has a sodium content of about 0.4% or less, such as, for example, Viscarin® XP (FMC Biopolymer).

In general, the biopolymer is present from about 5% to about 35% by weight in the pharmaceutical composition. In some preferred embodiments, the biopolymer is present from about 10% to about 25% by weight in the pharmaceutical composition. The amount of polymer in the pharmaceutical compositions can vary with, for example, the therapeutic agent and the absorption enhancer.

The therapeutic agent to biopolymer molar ratio can be from about 5:1 to 1:5, preferably about 2:1. In some instance, for example, if a cationic molecule is used as a binding agent, then the therapeutic agent (e.g., an antimicrobial agent) to cationic molecule molar ratio can be from about 1:4 to 1:1, preferably from about 1:2 to 1:1, e.g., 1:2 for antimicrobial agent:amino acid embodiments and 1:1 for antimicrobial agent:cetyl pyridinium embodiments.

In some embodiments, polycarbophil polymers (PCP) are preferred. An example of a preferred PCPs include AA1 (Noveon™).

In some embodiments Carbopol polymers are preferred. Example of preferred Carbopols include Carbopol 974 (Noveon™) and carbopol 971 (Noveon™).

Absorption Enhancers:

As used herein, the term "absorption enhancer" shall mean any substance which is effective to increase the absorption of a therapeutic agent through the mucosa relative to absorption without such agent.

The pharmaceutical compositions of the present invention generally include an absorption enhancer, such as a polyoxyethylene (POE), for example a polyoxyethylene alkyl ether or polyoxyethylene ester, a fatty acid, for example a mono-, di-, or tri-glyceride of a fatty acid, a salt of a fatty acid, a fatty alcohol, a lipid, or a polymer or antimicrobial agent having lipid-like properties. In some preferred embodiments, the invention includes a polyoxyethylene (POE) alkyl ether.

Frequently used absorption enhancers include for example, lipids, Gelucire, Gelmul, capric and caprylic acids, oleic acids, palmitic acids, stearic acids, Capmuls, for example, CAPMUL MCM 90 (a mixture of mono- and di-glycerides of saturated $C_8$-$C_{10}$ fatty acids with monoglyceride; Abitec, Corp.) CAPMUL 8210 (similar to MCM, but with about 70% monoglycerides) or Capmul C10. Gelicure is commercially available, for example, from GatteFosse Corporation (Westwood, N.J.). Gelmul is commercially available, for example Gelmul 90. Captex is commercially available, for example, Captex 1000 and Captex 100.

In some instances, a polyoxyethylene (POE) alkyl ether is a preferred absorption enhancer, for example, a polyoxyethylene (POE) alkyl ether having an alkyl chain length units from about 4 to about 23. A POE alkyl ether has the formula $R(OCH_2CH_2)_nOH$, where n refers to the number of oxyethylene units, and R refers to an alkyl moiety having a defined number of carbons.

In some embodiments, where the POE is a POE ester, R refers to the acyl moiety attached to the POE.

In one aspect, the oxyethylene unit (defined above as n) is from about 4 to about 23 units, preferably 10 to 15 units.

Examples of polyoxyethylene (POE) alkyl ethers include an alkyl moiety (R above) having from about 12 to about 22 carbons. Examples of POE alkyl ethers include lauryl, cetyl and oleyl alkyl ethers, such as laureth-12, ceteth-12, ceteth-15, and oleth-10.

A "Laureth" POE alkyl ether enhancer is meant to convey an enhancer of the following structure: $C_{12}H_{25}(OCH_2CH_2)_nOH$, wherein n is as described above. When the Laureth POE alkyl ether enhancer is denoted with a number (e.g. Laureth-12; Laureth-4 etc.), the number following the term Laureth denotes the number of oxyethylene units. For example, a Laureth-12 POE alkyl ether enhancer is $C_{12}H_{25}(OCH_2CH_2)_{12}OH$.

An "Oleth" POE alkyl ether enhancer is meant to convey an enhancer of the following structure: $CH_3(CH_2)_7CH=CH(CH_2)_7CH_2(OCH_2CH_2)_nOH$, wherein n is as described above. When the Oleth POE alkyl ether enhancer is denoted with a number (e.g. Oleth-12; Oleth-10 etc.), the number following the term Oleth denotes the number of oxyethylene units. For example, an Oleth-12 POE alkyl ether enhancer is $CH_3(CH_2)_7CH=CH(CH_2)_7CH_2(OCH_2CH_2)_{12}OH$.

A "Ceteth" POE alkyl ether enhancer is meant to convey an enhancer of the following structure: $C_{16}H_{34}(OCH_2CH_2)_nOH$, wherein n is as described above. When the Ceteth POE alkyl ether enhancer is denoted with a number (e.g. Ceteth-12; Ceteth-4 etc.), the number following the term Ceteth denotes the number of oxyethylene units. For example, a Ceteth-12 POE alkyl ether enhancer is $C_{16}H_{34}(OCH_2CH_2)_{12}OH$.

A "Steareth" POE alkyl ether enhancer is meant to convey an enhancer of the following structure: $C_{18}H_{38}(OCH_2CH_2)_nOH$, wherein n is as described above. When the Steareth POE alkyl ether enhancer is denoted with a number (e.g. Steareth-12; Steareth-4 etc.), the number following the term Steareth denotes the number of oxyethylene units. For example, a Steareth-12 POE alkyl ether enhancer is $C_{18}H_{36}(OCH_2CH_2)_{12}OH$.

An "Octydodecyl" POE alkyl ether enhancer is meant to convey an enhancer of the following structure: $C_{20}H_{42}(OCH_2CH_2)_nOH$, wherein n is as described above. When the Octydodecyl POE alkyl ether enhancer is denoted with a number (e.g. Octydodecyl-12; Octydodecyl-4 etc.), the number following the term Octydodecyl denotes the number of oxyethylene units. For example, an Octydodecyl-12 POE alkyl ether enhancer is $C_{20}H_{42}(OCH_2CH_2)_{12}OH$.

A "Cholesteryl" POE alkyl ether enhancer is meant to convey an enhancer of the following structure:

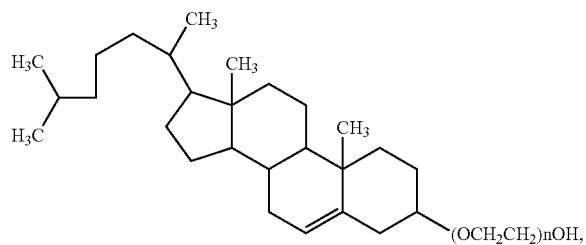

wherein n is as described above. When the Cholesteryl POE alkyl ether enhancer is denoted with a number (e.g. Cholesteryl-12; Cholesteryl-4 etc.), the number following the term Cholesteryl denotes the number of oxyethylene units. For example, a Cholesteryl-12 POE alkyl ether enhancer is

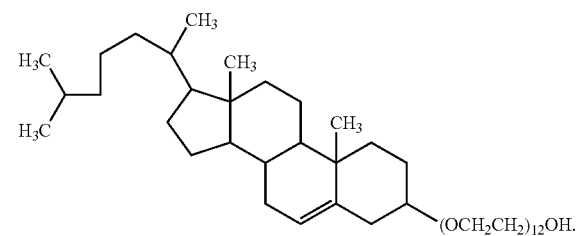

An "Isosteareth" POE alkyl ether enhancer is meant to convey an enhancer of the following structure: $(CH_3)_2CH(CH_2)_{15}(OCH_2CH_2)_nOH$, wherein n is as described above. When the Isosteareth POE alkyl ether enhancer is denoted with a number (e.g. Isosteareth-12; Isosteareth-4 etc.), the number following the term Isosteareth denotes the number of oxyethylene units. For example, a Isosteareth-12 POE alkyl ether enhancer is $(CH_3)_2CH(CH_2)_{15}(OCH_2CH_2)_{12}OH$.

An "Isoceteth" POE alkyl ether enhancer is meant to convey an enhancer of the following structure: $(CH_3)_2CH(CH_2)_{13}(OCH_2CH_2)_nOH$, wherein n is as described above. When the Isoceteth POE alkyl ether enhancer is denoted with a number (e.g. Isoceteth-12; Isoceteth-4 etc.), the number following the term Isoceteth denotes the number of oxyethylene units. For example, a Isoceteth-12 POE alkyl ether enhancer is $(CH_3)_2CH(CH_2)_{13}(OCH_2CH_2)_{12}OH$.

A "Beheneth" POE alkyl ether enhancer is meant to convey an enhancer of the following structure: $C_{22}H_{45}(O)(OCH_2CH_2)_nOH$, wherein n is as described above. When the Beheneth POE alkyl ether enhancer is denoted with a number (e.g. Beheneth-12; Beheneth-4 etc.), the number following the term Beheneth denotes the number of oxyethylene units. For example, an Beheneth-12 POE alkyl ether enhancer is $C_{22}H_{45}(OCH_2CH_2)_{12}OH$.

In some embodiments, the polyoxyethylene (POE) alkyl ether has an oxyethylene unit (n) of from about 4 to about 23 units (e.g., from about 8 to about 20 units, such as from about 10 to about 15 units) and has an alkyl moiety (R) of from about 12 to about 22 carbons (e.g., from about 12 to about 18 carbons), for example, 12, 16, 18, 20 or 22 carbons. In a preferred embodiment, the POE alkyl ether has an oxyethylene unit (n) of from about 8 to about 20 units and (R) of from about 12 to about 18 carbons. More preferably, the POE alkyl ether has an oxyethylene unit (n) of from about 10 to about 15 units and an alkyl moiety (R) of from about 12 to 18 carbons.

In some instances a fatty acid or fatty alcohol is an absorption enhancer. In one aspect, the fatty acid or fatty alcohol has a carbon chain length of from about 10 to about 18 carbons. In another aspect of the invention, the carbon chain length is from about 12 to about 16 carbons.

In some instances, a fatty acid salt is used as an absorption enhancer, for example, sodium laurate, sodium hexanoate, sodium caprylate, sodium decanoate, and sodium myristate. Preferably, the fatty acid salt is sodium laurate.

In some instances, a combination of two or more enhancers is used in a pharmaceutical composition. For example, a combination of two fatty acid salts can be used or a combination of a POE enhancer with a fatty acid or another POE.

In general, the absorption enhancer is present in the pharmaceutical composition from between about 35% to about 85% by weight, preferably from about 50% to about 75%.

The ratio of the absorption enhancer to the therapeutic agent is generally from about 10:1 (absorption enhancer:therapeutic agent) to about 1:2 (absorption enhancer:therapeutic agent). For example, the ratio can be about 10:1, 9:1, 8:1, 7:1, 6:1, 5:1, 4:1, 3:1, 2:1, 1:1, or 1:2. In some preferred embodiments, the ratio of absorption enhancer to therapeutic agent is between about 5:1 and about 1:1. In another preferred embodiment the ratio of absorption enhancer to therapeutic agent is about 4:1 or about 2:1.

The preferred ratio of absorption enhancer to therapeutic agent can vary depending on a number of factors, including the nature of the therapeutic agent, the nature of the absorption enhancer, the nature of the biopolymer, and the nature and/or presence or absence of a salt or ion.

Alternatively, any known absorption enhancers may be used, including any mixtures of the above.

Salts and/or Charged Ions

In some embodiments, the pharmaceutical compositions include a salt or other charged ion. For example, a pharmaceutical composition can include a cationic agent such as a positively charged metal ion, or any charged cationic molecules, such as, for example, calcium, potassium, magnesium, lithium, iron, copper, zinc, sodium, aluminum, manganese, chromium, cobalt, nickel, ammonium salts, quaternary ammonium salts such as benzalkonium derivatives, cetyl pyridinium derivatives, dodecyl-trimethyl ammonium salt derivatives, tetradecyl-trimethyl ammonium salt derivatives and cetyl-trimethyl ammonium salt derivatives. Additionally, basic amino acids such as arginine, lysine and histidine can be included. Preferred metal cations include, for example, calcium, potassium, magnesium, iron, copper, zinc, aluminum, manganese, chromium, cobalt, nickel, and/or sodium.

Surfactants

In some instances, the pharmaceutical composition includes one or more surfactants. For example, the composition can include simethecone, SDS, or another surfactant.

Other Ingredients

The tablets and capsules of the invention can contain, in addition to the active ingredients, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants for example, magnesium stearate, polyethylene glycol, silica or talc; disintegrants, for example, potato starch, flavoring or coloring agents, or acceptable wetting agents. Oral liquid preparations generally may be in the form of aqueous or oily solutions, suspensions, emulsions, syrups or elixirs, and may contain conventional additives such as suspending agents, emulsifying agents, non-aqueous agents, preservatives, coloring agents and flavoring agents. In either case, the composition is designed such that the therapeutic agent (e.g., antimicrobial agent) may be transmucosally delivered into the bloodstream, preferably through the walls of the small intestines.

Coatings

In some embodiments, the compositions of the invention are formulated with enteric coatings in order to prevent the degradation of the therapeutic agent by the acidity of the gastric fluid and optimize delivery of the active agent to the desired location in the intestine. Capsules can be coated with selected materials depending upon the desired capsule characteristics, and may include, for example, cellulose acetate phthalate, hydroxypropyl methylcellulose phthalate, polyvinyl acetate phthalate, shellac, methacrylic acid and esters thereof, zein, or other materials known in the art. The enteric coating materials may be applied with or without plasticizers, such as acetylated glycerides, triethyl citrate, propylene glycol or diethylphthalates. Preferred coating materials are those which dissolve at a pH of 5 or above. The coatings therefore only begin to dissolve when they have left the stomach and entered the small intestine. A thick layer of coating can be provided which will dissolve in about fifteen minutes thereby allowing the capsule underneath to breakup only when it has reached the duodenum. Such a coating can be made from a variety of polymers such as cellulose acetate trimellitate (CAT), hydroxypropylmethyl cellulose phthalate (HPMCP), polyvinyl acetate phthalate (PVAP), cellulose acetate phthalate (CAP) and shellac as described by Healy in his article "Enteric Coatings and Delayed Release" Chapter 7 in Drug Delivery to the Gastrointestinal Tract, editors Hardy et al., Ellis Horwood, Chichester, 1989. For coatings of cellulose esters, a thickness of 200-250 μm would be suitable.

Examples of preferred materials include methylmethacrylates or copolymers of methacrylic acid and methylmethacrylate. Such materials are available as EUDRAGIT™ polymers (Rohhm Pharma, Darmstadt, Germany). Eudragits are copolymers of methacrylic acid and methylmethacrylate. Preferred compositions are based on EUDRAGIT L 30 D-55, EUDRAGIT L1W-55, EUDRAGIT m L100 and EUDRAGIT S100. EUDRAGIT L30-D55 AND L1W-55 dissolve at pH>5.5. EUDRAGIT™ L100 dissolves at pH 6 and upwards and comprises 48.3% methacrylic acid units per g dry substance; EUDRAGIT™ S100 dissolves at pH 7 and upwards and comprises 29.2% methacrylic acid units per g dry substance. Preferred coating compositions are based on EUDRAGIT™ L100 and EUDRAGIT™ S100 in the range 100 parts L100:0 parts S100 to 20 parts L100:80 parts S100. The most preferable range is 70 parts L100:30 parts S100 to 80 parts L100:20 parts S100. As the pH at which the coating begins to dissolve increases, the thickness necessary to achieve colon specific delivery decreases. For formulations where the ratio of EUDRAGIT™ L100:S100 is high, a coat thickness of the order 150-200 μm is preferable. This is equivalent to 70-110 mg of coating for a size 0 capsule. For coatings where the ratio EUDRAGIT™ L100:S100 is low, a coat thickness of the order 80-120 μm is preferable, equivalent to 30 to 60 mg coating for a size 0 capsule.

Formulations

The pharmaceutical compositions described herein can be formulated, for example, as a solid, semi-solid, or liquid.

The pharmaceutical compositions of this invention may be orally administered in any orally acceptable dosage form including, but not limited to, capsules, tablets, emulsions and aqueous suspensions, dispersions and solutions. For pediatric and geriatric applications, emulsions, suspensions, syrups and chewable tablets may be especially suitable. In the case of tablets for oral use, carriers which are commonly used can include lactose and corn starch. Lubricating agents, such as magnesium stearate, can also be added. For oral administration in a capsule form, useful diluents can include lactose and dried corn starch. When suspensions and/or emulsions are administered orally, the active ingredient may be suspended or dissolved and combined with emulsifying and/or suspending agents. If desired, certain sweetening and/or flavoring and/or coloring agents may be added.

Dosage Regimes

The compositions described herein can, for example, be administered orally. In general, a dosage ranging from about 0.001 to about 100 mg/kg of body weight, e.g., between 0.001-1 mg/kg, 1-100 mg/kg, or 0.01-5 mg/kg, every 4 to 120 hours, e.g., about every 6, 8, 12, 24, 48, or 72 hours, or according to the requirements of the particular compound. For example, the compound can be administered having a dose of about 250 mg therapeutic agent such as ceftriaxone. Typically, the pharmaceutical compositions of this invention will be administered from about 1 to about 6 times per day. The amount of active ingredient that may be combined with the carrier materials to produce a single dosage form will vary depending upon the host treated and the particular mode of administration. A typical preparation will contain from about 5% to about 95% therapeutic agent (w/w). Alternatively, such preparations contain from about 20% to about 80% therapeutic agent.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Combination Therapies

In some instances, the pharmaceutical compositions described herein can include more than one therapeutic agent, for example, having a plurality of therapeutic agents in a single composition. For example, a pharmaceutical composition described herein can include an antimicrobial agent in combination with an anti-inflammatory agent, and/or an analgesic agent, and or an additional antimicrobial agent. When the compositions of this invention include a combination of a compound of the formulae described herein and one or more additional therapeutic or prophylactic agents, both the compound and the additional compound may be present at dosage levels of between about 1 to 100%, and more preferably between about 5 to 95% of the dosage normally administered in a monotherapy regimen. In other instances, the pharmaceutical compositions described herein can be administered with another pharmaceutical composition. For example, the pharmaceutical composition can be administered in conjunction with an additional pharmaceutical composition that includes an additional therapeutic agent.

The combinations of therapeutic agents can be administered either together, for example, at the same time in separate formulations or in a single formulation; or they can be administered separately, for example, administering a dose of a first pharmaceutical composition at a first time and administering a dose of a second pharmaceutical composition at a second, different time.

Methods of Treatment:

In general, the pharmaceutical compositions described herein can be used to treat or prevent one or more diseases or disorders in a subject. In particular, the pharmaceutical compositions can be used to treat an infection, for example an antimicrobial infection, in a subject. For example, a pharmaceutical composition including a cephalosporin such as ceftriaxone can be administered to a subject to treat an infection. Other antimicrobials useful in the pharmaceutical compositions described herein to treat infection include daptomycin, cidofovir, meropenem, and caspofungin.

The methods include administering to a human or other animal a therapeutically or prophylactically-effective amount of the therapeutic agent. "Therapeutically effective amount" means an amount of the therapeutic agent sufficient to prevent the onset, alleviate the symptoms, or stop the progression of a condition, disorder or disease, for example, a microbial infection. The compositions of the invention can be administered as a single daily dose or in multiple doses per day.

In certain embodiments, the compositions of the invention can be used to treat respiratory tract infections, skin and soft tissue infections, urinary tract infections, sinusitis, sexually transmitted diseases, endocarditis, bacteremia, osteomyelitis, septicemia and lyme disease.

Methods of Making

The pharmaceutical compositions described herein can be made in a variety of ways. For example, in some instances, the compositions can be prepared by hydrating a biodegradable polymer with a therapeutic agent in water followed by lyophilization. The lyophilized complex is then ground into finer particles using a high shear mixer, and then granulated with an absorption enhancer. The granulations can then be filled, for example, into a gelatin capsule.

Other methods of making a pharmaceutical composition described herein include spray drying/congealing, forming an emulsion of therapeutic agent and biopolymer, and other techniques known to those skilled in the art.

Bioavailability

In some instances, the compositions described herein are orally bioavailable. For example, a composition can have an oral bioavailability from about 5% to about 95%, e.g., about 10%, 20%, 35%, 50%, 55%, 60%, 70%, or 80%.

In some preferred embodiments, a therapeutic agent in a composition described herein has a bioavailability that is greater than the bioavailability of a therapeutic agent in the absence of an enhancer (i.e., an absorption enhancer). For example, the bioavailability can be about 1.5 times the bioavailability in the absence of an enhancer. Preferably, the bioavailability of a therapeutic agent is about 2 times, 3 times, 4 times, 5 times, 10 times, 15 times, 20 times, 50 times or greater than the bioavailability of the therapeutic in the absence of an enhancer.

In some preferred embodiments, where the enhancer (i.e., absorption enhancer) is a POE (e.g., a POE alkyl ether), the bioavailability of the therapeutic agent is at least about 1.5 times the bioavailability of the therapeutic agent in a composition with another enhancer (e.g., a fatty acid enhancer). Preferably, the bioavailability of the therapeutic agent is about 2 times, 3 times, 5 times, 10 times, 15 times, 20 times, 50 times or greater than the bioavailability of the therapeutic agent in a composition with another enhancer.

Some useful compositions of the invention include: a composition comprising ceftriaxone, Capmul C10 and carrageenan; a composition comprising ceftriaxone, Gelmul 90 and carrageenan; a composition comprising ceftriaxone, Captex 100 and carrageenan, a composition comprising an antimicrobial such as daptomycin, diofovir, 7-(((5-amino-1,2,4-thiadiazol-3-yl)-(Z)-(fluoromethoxyimino)acetyl)amino)-3 (E)-((imino-1-piperazinylmethyl)-methylhydrazono) methyl-3-cephem-4-carboxylic acid, meropenem, capsofungin, or ceftriaxone, a POE absorption enhancer, and a biopolymer; a composition comprising ceftriaxone, a laureth containing POE such as laureth 12, and carrageenan; a composition comprising ceftriaxone, a ceteth containing POE such as ceteth 10, and carrageenan; a composition comprising ceftriaxone, an oleth containing POE such as oleth 10, and carrageenan; a composition comprising ceftriaxone, a steareth containing POE such as steareth 10, and carrageenan; a composition comprising ceftriaxone, an octyldodecyl containing POE, and carrageenan; a composition comprising ceftriaxone, cholesteryl, and carrageenan. The number of oxyethylene units of a POE can vary, for example from between 4 and 23 repeat units. The ratio of enhancer to therapeutic agent ratio can vary, for example from between 6:1 to about 1:1, preferably from about 4:1 to about 2:1, such as 4:1 or 2:1. In some instances, the biopolymer in the compositions described above is other than carrageenan, for example, the biopolymer can be a cellulosic such as hydroxyethylcellulose, or a carbopol, or a polycarbophil.

EXAMPLES

Example 1

Preparation of Therapeutic Compositions

Preparation of Ceftriaxone Pharmaceutical Composition Via Complex Formation or Ceftriaxone/Polymer Dry Blend (a) Preparation of Ceftriaxone/Polymer Complexes Ceftriaxone/Carrageenan Complex Preparation of the ceftriaxone/carrageenan complex was prepared by dissolving 10 mg of calcium chloride in 90 mL of purified water followed by hydrating 400 mg of the polymer (carrageenan) calcium chloride/purified water solution. Once the polymer was hydrated, 10 mL of a 100 mg/mL ceftriaxone solution in purified water was added to the polymer solution yielding a final ceftriaxone solution concentration of 10 mg/mL. The complex solution was frozen at −80° C. then lyophilized to dryness according to the cycle parameters shown in Table 1. The lyophilized complex was further ground into a fluffy, light yellow powder using a mini-blender. The complex was stored in amber glass jars at −20° C.

Ceftriaxone/Hydroxyethyl Cellulose Complex (CTX/HEC); Ceftriaxone/Polycarbophil (CTX/PCP) Complex: Ceftriaxone/Carbopol (CTX/CP) Complex Complexes of ceftriaxone and the polymers hydroxyethyl cellulose, polycarbophil and carbopol were prepared by hydrating the desired polymer in aqueous solution in purified water at 0.2-0.4% (w/v) followed by addition of a 100 mg/mL ceftriaxone solution in purified water to yield a final solution concentration of 10 mg/mL when added to the hydrated polymer. Complexes prepared with polycarbophil or carbopol required neutralization with 2N NaOH to pH 7.2 for hydration prior to addition of the stock ceftriaxone solution to the polymer. The complex solution was frozen at −40° C. then lyophilized to dryness according to the cycle parameters shown in Table 1. The lyophilized complex was further ground into a powder using a mini-blender. The complex was stored in amber glass jars at −20° C.

TABLE 1

Lyophilization Cycle Parameters for ceftriaxone/polymer complex

| Step | Temperature (° C.) | Time (hours) |
| --- | --- | --- |
| Pre-Freeze | −40 | 2 |
| Ramp | −10 | 0.5 |
| Hold | −10 | 8 |
| Ramp | +10 | 0.5 |
| Hold | +10 | 8 |
| Ramp | +25 | 0.5 |
| Hold | +25 | 8 |
| Ramp | +40 | 0.5 |
| Hold | +40 | 8 |
| Ramp | +25 | 0.5 |
| Hold | +25 | 12 |

Preparation of Ceftriaxone/Polymer Dry Blend

The dry blend of the formulation components is prepared by weighing out 1.2 grams of ceftriaxone sodium (equivalent to 1.0 gram of ceftriaxone) or other drug molecule, and 0.4 grams of carrageenan (or other polymer). The two dry components are mixed to form a homogeneous powder using a mini-blender. The drug/polymer powder is then granulated with the enhancer as described in section (b) below.

(b) Preparation of Ceftriaxone Pharmaceutical Compositions

Ceftriaxone formulations were prepared as granulations with the complex, dry blend of the components or ceftriaxone crystals. Granulations are characterized as combining a semi-solid enhancer with a ceftriaxone/polymer complex or dry blend (see 1(a)). Prior to preparation of the granulations, the enhancer was pre-melted in a water bath on a heater plate. The Enhancer: ceftriaxone granulations were prepared by weighing out the ceftriaxone/polymer complex or dry blend into a mini-blender container. The appropriate amount of enhancer was added to yield the specified enhancer to ceftriaxone/polymer complex or dry blend ratio. The components were blended together in the mini-blender until the granulation was uniform in appearance. The components were then cooled at −15° C. for 15-20 minutes to re-congeal, then ground into smaller particles using the mini-blender.

Preparation of Capsules for Administration in Rats

Capsules were prepared by filling the granulations of 1 (b) into #9el (extra long) hard gelatin capsules by use of a specially designed #9el filling funnel. The filling funnel is designed such that the capsule body sits in the base of the unit. The funnel is placed on top of the capsule body then the material is filled into the funnel and pushed down into the capsule. Capsule fill weight is based on the theoretical potency of the granulation or dry blend to yield 10 mg of ceftriaxone per capsule.

Example 2

Screening of Compositions Comprising Polyoxyethylene Alkyl Ether Enhancers

Screening of Compositions Comprising a Polyoxyethylene Alkyl Ether Enhancer and Ceftriaxone/Carrageenan Complex at 4:1 and 2:1 in Rats The following rat model was used to screen all therapeutic compositions tested:

Male Sprague Dawley rats weighing approximately 250 g with free access to water were fasted overnight. These rats were anesthetized with 40 mg/kg pentobarbital via jugular vein catheter. The small intestine was exposed by a ventral midline incision. A small incision was made into the duodenum and a #9el capsule was inserted into the lumen of the small intestine. The duodenum and the midline incisions were sutured closed. The rats regained consciousness in 30-90 minutes. Blood samples were taken from the jugular vein catheter at 0, 15, 30 and 60 minutes and 2, 3, 4 and 6 hours. Food was returned at 1 hour post surgery. Blood samples were collected in heparinized tubes and subsequently centrifuged. The plasma was stored at −20 C in heparinized tubes. The rats regained consciousness in 30-90 minutes. After the 6 hr blood sample, the rat was euthanized and a necropsy was performed to determine accuracy and integrity of the surgery. The duodenum was examined for blockage, leakage and any evidence of inflammation or irritation at the site of the capsule implantation.

Laureth POE Analogs

Compositions including a variety of Laureth POE analogs, including Laureth-4, -7, -9, -10, -12, -15, -20 and -23, were screened to compare the percent bioavailability of the various compositions in rats.

The compositions each included 21.4% ceftriaxone sodium; 7.2% polymer; 71.4% enhancer by weight, and were made according to the methods described in Example 1 (a) and (b).

The percent bioavailability in rats with the lauryl POE ether analogs are shown graphically in FIG. 1.

POE Alkyl Ether Derivatives

Compositions comprising ceftriaxone/carrageenan complex and a POE alkyl ether were prepared as described in Example 1. As shown in Tables 2 and 2.1, the POE alkyl ether enhancers had different alkyl moiety carbon lengths and different numbers of oxyethylene units ranging from POE oxyethylene units of 4 to 23 units and an alkyl moiety of 12 to 18 carbons. The ratio of enhancer:drug was 4:1 for these granulations with ceftriaxone/carrageenan complex.

The compositions disclosed in Tables 2 and 2.1 included, in each instance, 21.4% ceftriaxone sodium; 7.2% polymer; 71.4% enhancer, by weight. (Note: The ratio of drug to enhancer is determined by the weight of the drug, not the weight of the drug salt. Therefore, although the ratio of enhancer to drug salt is less than 4:1, the amount of enhancer to drug is 4:1.)

The percent bioavailabilty for each composition was determined via the rat model (vide supra).

The percent bioavailability results for enhancer:ceftriaxone/carrageenan at 4:1 are shown in Tables 2 and 2.1. The results show enhancers having POE oxyethylene units ranging from 10 to 20 units and an alkyl moiety of 12 to 18 carbons resulted in the greatest increase in ceftriaxone absorption when combined with the complex of ceftriaxone/carrageenan.

TABLE 2

Summary of % bioavailability results for enhancer:ceftriaxone/carrageenan granulations at a 4:1 (enhancer:ceftriaxone) ratio in rats

| Enhancer | Oxyethylene Units* | | | | |
|---|---|---|---|---|---|
|  | 4 | 5 | 7 | 9 | 10 |
| Laureth | 39 (16) |  | 54 (2) | 60 (19) |  |
| Ceteth |  |  |  |  | 59 (16) |
| Oleth |  |  |  |  | 73 (10) |
| Steareth |  |  |  |  | 60 (16) |
| Octyldodecyl |  | 10 (2) |  |  | 15 (4) |
| Cholesteryl |  |  |  |  | 32 (14) |

*Numbers in parentheses correspond to standard deviation.

TABLE 2.1

Summary of % bioavailability results for enhancer:ceftriaxone/carrageenan granulations at a 4:1 (enhancer:ceftriaxone) ratio in rats, continued

| Enhancer | Oxyethylene Units* | | | | |
|---|---|---|---|---|---|
|  | 12 | 15 | 16 | 20 | 23 |
| Laureth | 83 (24) | 30 (15) |  | 17 (6) | 10 (4) |
| Ceteth |  |  |  |  |  |
| Oleth |  |  |  | 62 (45) |  |
| Steareth |  |  |  | 65 (14) |  |
| Octyldodecyl |  |  |  |  |  |
| Cholesteryl |  | 31 (18) | 13 (4) |  |  |

*Numbers in parentheses correspond to standard deviation.

Several of the enhancers exhibited bioavailabilites ranging from 60-80%. Screening of the formulations possessing the highest bioavailabilities at 4:1 were evaluated at an enhancer:ceftriaxone/carrageenan ratio of 2:1 utilizing the same protocol above, but substituting compositions comprising enhancer:ceftriaxone/carrageenan complex of 2:1 for enhancer:ceftriaxone/carrageenan complex of 4:1. These compositions, in each instance, included 33.3% ceftriaxone sodium; 11.1% polymer; and 55.6% enhancer, by weight. The results of the compositions having a 2:1 ratio of enhancer to drug are presented in Table 3. (Note: As above, the ratio of drug to enhancer is determined by the weight of the drug, not the weight of the drug salt. Therefore, although the ratio of enhancer to drug salt is less than 2:1, the amount of enhancer to drug is 2:1.)

TABLE 3

Summary of % bioavailabillty results for enhancer:ceftriaxone/carrageenan granulations at a 2:1 (enhancer:ceftriaxone) ratio in rats

| Enhancer ID | Oxyethylene Units* | | | | |
|---|---|---|---|---|---|
|  | 8 | 10 | 12 | 15 | 20 |
| Laureth |  | 30 (8) | 38 (10) |  |  |
| Ceteth |  | 49 (14) | 43 (27) | 59 (20) |  |
| Oleth |  | 57 (20) | 43 (28) | 28 (11) | 11 (2) |
| Steareth | 31 (6) | 47 (19) |  | 36 (8) | 29 (8) |
| Isoceteth |  |  |  | 12 (8) |  |
| Isosteareth |  | 15 (6) |  | 16 (5) |  |
| Beheneth |  | 9 (4) |  |  | 7 (5) |

*Numbers in parentheses correspond to standard deviation.

The enhancer:ceftriaxone/carrageenan formulations resulting in the highest % bioavailabilities were Ceteth-10, 12 & 15, Oleth-10 & 12 and Steareth-10, all within the range form 40-60% bioavailability.

Example 3

Screening of Compositions Comprising Polymers as Alternatives to Carrageenan

Ceftriaxone was complexed with a polymer selected from hydroxyethyl cellulose (HEC) 250 L (non-ionic), hydroxyethyl cellulose 250H (non-ionic), carbopol (CP) 971(anionic), carbopol 974 (anionic) or polycarbophil (PCP) Noveon AA1 (anionic) as described in Example 1 to form a ceftriaxone/polymer complex. The complexes with the various polymers were prepared at polymer levels of A % and B % (vide infra) in the lyophilized form.

Compositions comprising the various ceftriaxone/polymer complexes and an enhancer were prepared in either a 4:1 or 2:1 ratio of enhancer to ceftriaxone/polymer complex as described in Example 1. For the polymer percent designated A % in the table @4:1, the composition included 22.2% drug salt; 3.7% polymer; and 74.1% enhancer. For the polymer percent designated B % in the table @4:1, the composition included 21.4% drug salt; 7.2% polymer; and 71.4% enhancer. For the polymer percent designated A % in the table @2:1, the composition included 35.3% drug salt; 5.9% polymer; and 58.8% enhancer. For the polymer percent designated B % in the table @2:1 the composition included 33.3% drug salt; 11.1% polymer; and 55.6% enhancer.

Each complex was administered intraduodenally (ID) as described in Example 2 above. The bioavailability of each of the formulations was compared with formulation standard Laureth-12:ceftriaxone/carrageenan at 4:1. The compositions and bioavailability results are summarized in Table 4.

TABLE 4

Summary of % bioavailability for POE enhancer:polymer
complex formulation screening in rats
% Bioavailability results for ceftriaxone-polymer complexes granulated
with various POE enhancers in rats (enhancer:ceftriaxone) ratio
(in the table, ceftriaxone is designated as CTX)

| | | Enhancer Type* | | | | |
|---|---|---|---|---|---|---|
| Complex ID | Percent Polymer | Laureth-12 @ 4:1 | Laureth-12 @ 2:1 | Ceteth-12 @ 2:1 | Ceteth-15 @ 2:1 | Oleth-10 @ 2:1 |
| CTX-HEC 250L | A | 70 (13) | 21 (10) | NT | NT | NT |
| | B | 48 (12) | 34 (27) | 56 (4) | 30 (6) | 32 (19) |
| CTX-HEC 250H | A | 68 (21) | NT | NT | NT | NT |
| | B | 56 (17) | 28 (8) | NT | NT | NT |
| GTX-CP 971 | A | 69 (27) | 30 (19) | NT | NT | NT |
| | B | 74 (24) | 37 (21) | NT | 46 (30) | 36 (22) |
| CTX-CP 974 | A | 58 (19) | 20 (5) | NT | NT | NT |
| | B | 47 (29) | 13 (5) | 40 (16) | NT | NT |
| CTX-PCP | A | 61 (9) | 18 (8) | NT | NT | NT |
| | B | 50 (20) | 47 (22) | 54 (10) | 26 (4) | 39 (15) |

*Numbers in parentheses in the columns corresponding to Enhancer Type correspond to standard deviation.

The results for the Laureth-12:polymer granulations at 4:1 demonstrate high percent bioavailabilities for several of the formulations. Screening was continued with the Laureth-12:polymer formulations which exhibited the highest bioavailability but at a 2:1 ratio. The percent bioavailability results for 2:1 ratio formulations were lower than those achieved for the 4:1 ratio. The highest % bioavailability achieved at 2:1 was the Laureth-12: ceftriaxone-PCP complex (47%). Screening at a 2:1 ratio with the best Laureth-12:polymer complex formulations was continued with other POE alkyl ether enhancers. The formulations which resulted in the highest bioavailabilities were Ceteth-12:ceftriaxone-HEC 250 L (B %), Ceteth-12:ceftriaxone-CP-974 (B %) and Ceteth-15:ceftriaxone-CP 971 (B %) at 56%, 54%, and 46%, respectively.

Example 4

Study of Ceteth-12:ceftriaxone-polycarbophil (PCP) in the Intestinal Lumen

Figure 2:
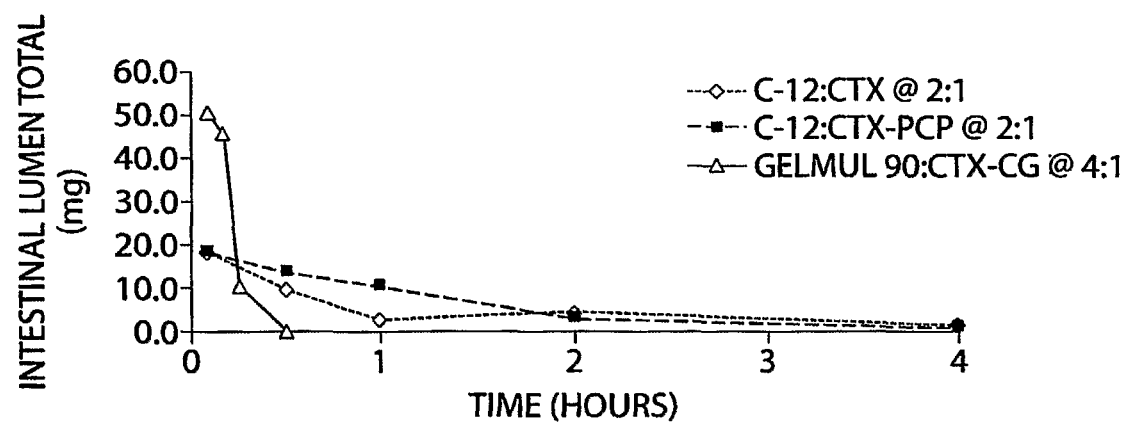
FIG. 2 is a graph depicting intestinal lumen content of enhancer in rat after ID dosing.

An intestinal lumen study was conducted as described in Example 2 to determine if the Ceteth-12 (C-12):ceftriaxone-PCP complex formulation at a 2:1 ratio described in Example 3 exhibited different absorption and breakdown of the ceftriaxone and Ceteth-12 components in the intestines. The results obtained for the ceftriaxone and Ceteth-12 (C-12) in the plasma are shown in FIG. 2.

Ceteth-12 formulations resulted in significantly greater amounts of ceftriaxone in the plasma over time. The attached graph/figure shows the monoglyceride Gelmul 90 at a 4:1 Gelmul:Cefiriaxone ratio has a shorter residence time in the rat small intestine lumen than the POE alkyl ether in a 2:1 Ceteth-12:Ceftriaxone formulations. The 4:1 Gelmul:Ceftriaxone formulations resulted in an average bioavailability of 30% whereas the 2:1 Ceteth12:Ceftriaxone-PCP formulations resulted in an average bioavailability of 54%.

Example 5

Oral Bioavailability of Ceftriaxone in Man

A single center, nonrandomized trial in which male subjects received an intravenous dose followed by administration of five oral formulations of ceftriaxone was conducted. The mean ceftriaxone dose was 245 mg. These formulations were placed in a mechanical capsule (Enterion™) commonly used in scintigraphy studies. Upon reaching the proximal small bowel, the capsule was opened non-invasively via an external electrical signal and serial blood sampling was initiated to study drug absorption up to and including 24 hours post-capsule activation. There was a 5 day washout period between each treatment. The oral ceftriaxone formulations studied are in the Table 5 below. The oral bioavailability of ceftriaxone without any absorption enhancer is approximately 0-5%. There were no deaths or serious adverse events. There were no clinically significant changes in vital signs or ECGs that were attributable to study drug.

The oral ceftriaxone formulations included: T-2, Ceteth-12:ceftriaxone complex (2:1), T-3, Oleth-10:ceftriaxone complex (2:1), T-4, Laureth-12:ceftriaxone complex (2:1), T-5, Ceteth-12:ceftriaxone complex (1:1) and T-6, Ceteth-12: ceftriaxone/polycarbophil dry blend (2:1). Upon reaching the proximal small bowel, the Enterion™ capsule was opened non-invasively via an external signal and serial blood sampling was initiated to study drug absorption up to and including 24 hours post-capsule activation.

TABLE 5

Percent bioavailability of oral ceftriaxone formulations

| | CTX, Na (mg) | Enhancer (mg) | Enhancer Type | Polymer (mg) | Polymer Type | % Bioavailability (SD) |
|---|---|---|---|---|---|---|
| T-1 | 308.6[1] | 0 | — | 0 | — | 100 |
| T-2 | 308.6[2] | 500 | Ceteth-12 | 100.6 | PCP[4] | 29.01 (13.95) |
| T-3 | 308.6[2] | 500 | Oleth-10 | 99.3 | CGN[5] | 11.38 (7.05) |
| T-4 | 308.6[2] | 500 | Laureth-12 | 99.3 | CGN[5] | 7.98 (2.99) |
| T-5 | 308.6[2] | 250 | Ceteth-12 | 100.1 | PCP[4] | 9.03 (1.23) |
| T-6 | 308.6[3] | 500 | Ceteth-12 | 100.0 | PCP[4] | 20.93 (8.81) |

[1]308.6 mg of CTX, Na = 250 mg CTX
[2]CTX, Na + polymer + CaCl$_2$ or NaOH (as a pH adjuster) in a lyophilized complex granulated with an enhancer
[3]CTX, Na + polymer are dry blended then granulated with Ceteth-12
[4]PCP = polycarbophil
[5]CGN = carrageenan

Example 6

Study of effect of enhancer on the bioavailability of daptomycin, 7-(((5-amino-1,2,4-thiadiazol-3-yl)-(Z)-(fluoromethoxyimino)acetyl)amino)-3 (E)-((imino-1-piperazinylmethyl)-methylhvdrazono)methyl-3-cephem-4-carboxylic acid, and ceftriaxone/carrageenan Daptomycin, 7-(((5-amino-1,2,4-thiadiazol-3-yl)-(Z)-(fluoromethoxyimino)acetyl)amino)-3(E)-((imino-1-piperazinylmethyl)-methylhydrazono)methyl-3-cephem-4-carboxylic acid (CMPD 1), and ceftriaxone were tested to compare the bioavailability using a POE alkyl ether enhancers versus other enhancers such as Gelmul 90, Capmul C10 and Sodium Laurate. The compositions, in each instance, included 21.4% drug salt; 7.2% polymer; 71.4% enhancer, by weight. (Note: The ratio of drug to enhancer is determined by the weight of the drug, not the weight of the drug salt. Therefore, although the ratio of enhancer to drug salt is less than 4:1, the amount of enhancer to drug is 4:1.)

In each instance, the compositions were administered ID in 3 rats, unless otherwise indicated. Cmax was determined as described in Example 2. The results are shown in Table 6 below:

TABLE 6

Comparison of Enhancer Effect on Daptomycin, CMPD 1 and ceftriaxone/carrageenan
Oral Absorption
Comparison of Enhancer Effect on Daptomycin, CMPD 1 and ceftriaxone:carrageenan complex
Oral Absorption

| | $Cmax^1$ (µg/mL) | | |
|---|---|---|---|
| Enhancer[5] | Daptomycin[2] Mean (±SD) | CMPD 1[3] Mean (±SD) | ceftriaxone/carrageenan complex[4] Mean (±SD) |
| Laureth-12 | 18 (12) | 22 (4) | 76 (18)[6] |
| Gelmul 90 | 6 (3) | 13 (8) | 51 (15)[7] |
| Capmul C10 | 7 (0.4) | 7 (7) | 26 (15)[8] |
| Sodium Laurate | 8 (3) | 7 (1) | 21 (17) |

[1]Cmax normalized to 40 mg/Kg. All data was generated using the rat model in Example 2.
[2]Enhancer granulated with lyophilized daptomycin (no polymer or cation)
[3]Enhancer granulated with lyophilized CMPD 1 (no polymer or cation)
[4]Enhancer granulated with ceftriaxone/carrageenan complex ("complex" is lyophilized ceftriaxone + polymer + cation)
[5]Enhancer:drug ratio = 4:1 in all studies
[6]16 rats
[7]6 rats
[8]10 rats

Example 7

Comparison of Percent Bioavailability of Therapeutic Compositions with and without a POE Enhancer Compositions including ceftriaxone, daptomycin, cidofovir, 7-(((5-amino-1,2,4-thiadiazol-3-yl)-(Z)-(fluoromethoxyimino)acetyl)amino)-3(E)-((imino-1-piperazinylmethyl)-methylhydrazono)methyl-3-cephem-4-carboxylic acid, meropenem, and caspofungin were prepared with and without a POE enhancer. As shown in Table 7, in most instances, the bioavailability of the compositions including the POE enhancer was greater than 25%, and in some instances even higher.

Ceftriaxone was present in the same percentages as Example 6 above. The formulation included ceftriaxone/carrageenan complex+Laureth-12 as the enhancer.

Daptomycin was present in the same percentages as Example 6 above. The formulation consisted of daptomycin carrageenan complex+Ceteth-15 as the enhancer Cidofovir was drug and enhancer only. The percentage included 23.8% drug and 76.2% Ceteth-12 as the enhancer, by weight.

7-(((5-amino-1,2,4-thiadiazol-3-yl)-(Z)-(fluoromethoxyimino)acetyl)amino)-3 (E)-((imino-1-piperazinylmethyl)-methylhydrazono)methyl-3-cephem-4-carboxylic acid was drug and enhancer only. The percentage included 21.9% drug and 78.1% Ceteth-15 as the enhancer, by weight.

Meropenem was drug and enhancer only. The percentage included 25% drug and 75% Ceteth-12 as the enhancer, by weight.

Caspofungin was drug and enhancer only. The percentage included 38.5% drug and 61.5% Ceteth-12 as the enhancer, by weight.

In each instance, the compositions were administered ID as described in Example 2 above.

TABLE 7

Percent bioavailability of therapeutic compositions with and without a POE alkyl ether enhancer

| | Drug only % BA | Drug plus enhancer[1] % BA |
|---|---|---|
| Ceftriaxone | 2 | 83[2] |
| Daptomycin | —* | 44[2] |
| Cidofovir | 2 | 44 |
| CMPD 1 | —* | 30 |
| Meropenem | 1 | 28 |
| Caspofungin | <1 | <5 |

[1]All compounds were formulated at a 4:1 (enhancer:drug) ratio
[2]Enhancer plus drug complex
*Compound known to have poor oral bioavailability.

A number of embodiments of the invention have been described. Nevertheless, it will be understood that various modifications may be made without departing from the spirit and scope of the invention. Accordingly, other embodiments are within the scope of the following claims.

The invention claimed is:

1. A method of formulating an orally administered therapeutic agent for increased oral bioavailability of the therapeutic agent in a subject, the method comprising
    a. combining in a pharmaceutical composition a biopolymer, a therapeutic agent and an absorption enhancer consisting of a Ceteth-12 polyoxyethylene alkyl ether; and
    b. formulating a therapeutically effective amount of the pharmaceutical composition in a dosage form suitable for oral administration to a subject in need thereof.

2. The method of claim 1, wherein the pharmaceutical composition results in an oral bioavailability of the therapeutic agent in the subject that is at least about 1.5 times greater than the bioavailability of the therapeutic agent in the subject when the therapeutic agent is orally administered to the subject in the absence of the absorption enhancer.

3. The method of claim 1, wherein the molar ratio of the therapeutic agent to the biopolymer in the pharmaceutical composition is about 5:1 to 1:5.

4. The method of claim 1, wherein the weight ratio of the absorption enhancer to the therapeutic agent in the pharmaceutical composition is about 10:1 to 1:2.

5. The method of claim 1, wherein the weight ratio of the absorption enhancer to the therapeutic agent in the pharmaceutical composition is about 2:1 to 4:1.

6. The method of claim 1, wherein the weight ratio of the absorption enhancer to the combination of the biopolymer and the therapeutic agent in the pharmaceutical composition is 2:1 to 4:1.

7. The method of claim 1, wherein the biopolymer is present in the pharmaceutical composition from about 5% to 35% by weight.

8. The method of claim 1, wherein the biopolymer is selected from the group consisting of a polysaccharide, a polycarbophil and a carbopol.

9. The method of claim 8, wherein the polysaccharide is a carrageenan.

10. The method of claim 1, wherein
   a. the biopolymer is a polycarbophil; and
   b. the weight ratio of the absorption enhancer to the therapeutic agent in the pharmaceutical composition is about 2:1.

11. The method of claim 10, wherein
   a. the weight ratio of the absorption enhancer to the combination of the biopolymer and the therapeutic agent in the pharmaceutical composition is about 2:1 to 4:1; and
   b. the biopolymer is present in the pharmaceutical composition from about 5% to 35% by weight.

12. The method of claim 1, wherein the pharmaceutical composition results in an oral bioavailability of the therapeutic agent in the subject that is greater than the oral bioavailability of the therapeutic agent in the subject when the therapeutic agent is orally administered to the subject in the absence of the biopolymer.

13. The method of claim 1, further comprising combining the biopolymer with the therapeutic agent to form a complex in a solution before combination with the absorption enhancer to form the pharmaceutical composition.

14. The method of claim 13, further comprising freezing and lyophilizing the complex prior to combination with the absorption enhancer to form the pharmaceutical composition.

15. The method of claim 1, wherein the pharmaceutical composition results in an oral bioavailability of the therapeutic agent in the subject that is at least about 10 times greater than the oral bioavailability of the therapeutic agent in the subject when the therapeutic agent is orally administered to the subject in the absence of the absorption enhancer.

16. A method of formulating an orally administered therapeutic agent for increased oral bioavailability of the therapeutic agent in a subject, the method comprising
   a. combining in a pharmaceutical composition a biopolymer, a cephalosporin therapeutic agent and an absorption enhancer consisting essentially of a polyoxyethylene alkyl ether having the formula $C_{16}H_{34}(OCH_2CH_2)_nOH$ where n is 4 to 23; and
   b. formulating a therapeutically effective amount of the pharmaceutical composition in a dosage form suitable for oral administration to a subject in need thereof.

17. The method of claim 16, wherein the pharmaceutical composition results in an oral bioavailability of the therapeutic agent in a subject that is greater than the bioavailability of the therapeutic agent the subject when the therapeutic agent is orally administered to the subject in the absence of the biopolymer.

18. The method of claim 16, further comprising combining the biopolymer with the therapeutic agent to form a complex in a solution before combination with the absorption enhancer to form the pharmaceutical composition.

19. The method of claim 18, further comprising freezing and lyophilizing the complex prior to combination with the absorption enhancer to form the pharmaceutical composition.

20. The method of claim 16, wherein the pharmaceutical composition results in an oral bioavailability of the therapeutic agent in the subject that is at least about 1.5 times greater than the oral bioavailability of the therapeutic agent in the subject when the therapeutic agent is orally administered to the subject in the absence of the absorption enhancer.

21. A method of treatment comprising orally administered to a subject a therapeutically effective amount of a pharmaceutical composition consisting essentially of a biopolymer, a therapeutic agent and an absorption enhancer consisting essentially of a Ceteth-12 polyoxyethylene alkyl ether.

22. The method of claim 21, wherein the pharmaceutical composition is produced by
   a. combining the biopolymer with a cephalosporin therapeutic agent to form a complex of the biopolymer and the cephalosporin therapeutic agent;
   b. combining in a pharmaceutical composition the complex and the polyoxyethylene alkyl ether absorption enhancer; and
   c. formulating a therapeutically effective amount of the pharmaceutical composition in a dosage form suitable for administration to a subject in need thereof.

23. The method of claim 21, wherein the weight ratio of the absorption enhancer to the complex in the pharmaceutical composition is about 1:1 to 4:1.

24. The method of claim 21, wherein the weight ratio of the therapeutic agent to the absorption enhancer in the pharmaceutical composition is about 2:1.

25. The method of claim 21, wherein the biopolymer is a polycarbophil.

26. The method of claim 25, wherein the weight ratio of the therapeutic agent to the absorption enhancer in the pharmaceutical composition is about 2:1.

* * * * *